United States Patent [19]

Uyeo et al.

[11] 4,081,443
[45] Mar. 28, 1978

[54] PENICILLIN OXIDES

[75] Inventors: Shoichiro Uyeo, Toyonaka; Hikaru Itani, Ibaraki; Tsutomu Aoki, Sennan; Teruji Tsuji, Takatsuki; Wataru Nagata, Nishinomiya, all of Japan

[73] Assignee: Shionogi & Co., Ltd., Osaka, Japan

[21] Appl. No.: 806,882

[22] Filed: Jun. 15, 1977

Related U.S. Application Data

[63] Continuation of Ser. No. 762,823, Jan. 25, 1977, abandoned.

[30] Foreign Application Priority Data

Jan. 29, 1976 Japan .................................. 51-8994

[51] Int. Cl.² .......................................... C07D 499/44
[52] U.S. Cl. .................................. 260/239.1; 424/271
[58] Field of Search ....................... 260/239.1, 306.7 C

[56] References Cited

U.S. PATENT DOCUMENTS 3,993,646  11/1976  Kamiya et al. .................... 260/239.1

Primary Examiner—Gerald A. Schwartz
Attorney, Agent, or Firm—Wenderoth, Lind & Ponack

[57] ABSTRACT

Compounds of the formula:

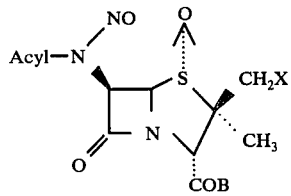

(where COB is carboxy or protected carboxy and X is hydrogen or nucleophilic group)

preparable by oxidation of the corresponding N-nitrosopenicillin derivatives are useful as starting materials for synthesizing known and useful cephalosporins.

10 Claims, No Drawings

PENICILLIN OXIDES

This is a continuation application of Ser. No. 762,823, filed Jan. 25, 1977, now abandoned.

This invention relates to 6-(N-nitro-N-acylamino)-penicillanic acid 1α-oxides and their derivatives. It further relates to a process for preparing penicillin 1α-oxides in high yield.

Compounds (I) according to this invention is represented by the following formula:

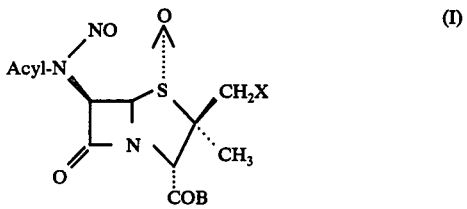

(where COB is carboxy or protected carboxy, and X is hydrogen or a nucleophilic group).

Acyl in Compounds (I) contains up to 25 carbon atoms and includes conventional acyls used in the chemistry of penicillins and cephalosporins, and is exemplified by an inorganic acyl including carbonic acyl (e.g. 2-8C alkoxycarbonyl, 8-15C aralkoxycarbonyl, 6-11C aryloxycarbonyl), and organic acyl including 1-5C alkanoyl, 3-8C cycloalkanoyl, 7-20C aralkanoyl, 7-10C aroyl, 1-5-C alkylsulfonyl, 6-10C arylsulfonyl, and 1-5C alkylphosphonyl.

These acyls, where possible, may have a hetero atom in the main nucleus, unsaturation, or substituent e.g. a halogen (e.g. fluorine, chlorine, bromine), nitrogen function (e.g. amino, hydrazo, azido, 1-5C alkylamino, 6-10C arylamino, 1-8C acylamino, 1-5C alkylideneamino, 1-8C acylimino, nitro), oxygen function (e.g. hydroxy, 1-5C alkoxy, 7-20C aralkoxy, 6-10C aryloxy, 1-8C acyloxy, oxo), sulfur function (e.g. mercapto, 1-5C alkylthio, 7-9C aralkylthio, 6-10C arylthio, 1-8C acylthio, thioxo, sulfo, sulfonyl, sulfinyl, 1-5C alkoxysulfonyl, 6-10C aryloxysulfinyl, carbon function (e.g. 1-5C alkyl, 1-5C alkenyl, 7-10C aralkyl, 6-10C aryl, carboxy, 2-6C carbalkoxy, carbamoyl, 1-8C alkanoyl, 7-11C aroyl, 1-5C aminoalkyl, 7-10C aralkanoyl, cyano), phosphorus function (e.g. phospho, phosphoroyl) or like substituents.

Representative Acyls include following groups:
1. 1-5C alkanoyl;
2. 2-5C haloalkanoyl;
3. azidoacetyl;
4. cyanoacetyl;
5. acyls of the formula:

(where Q and Q' each is hydrogen or methyl; and Ar is phenyl, dihydrophenyl, or a monocyclic heterocyclic aromatic group containing 1 to 4 hetero atoms selected from nitrogen, oxygen, and/or sulfur atoms, each optionally substituted by e.g. 1-5C alkyl, 1-5C alkoxy, halogen, trifluoromethyl, hydroxy, cyano, aminomethyl, nitroso, and nitro).

6. acyls of the formula:

(where G is oxygen or sulfur; and Ar, Q, and Q' are defined above);

7. acyls of the formula:

(where Ar is defined above; and T is
  i. amino, ammonio, amino protected by an amino-protecting group (including acyls e.g. benzyloxycarbonyl, 2-8C alkoxycarbonyl, cyclopentyloxycarbonyl, cyclohexyloxycarbonyl, benzhydryloxycarbonyl, cyclopropylmethoxycarbonyl, methanesulfonylethoxycarbonyl, 2,2,2-trichloroethoxycarbonyl, guanidylcarbonyl, substituted ureidocarbonyl, 1-5C alkanoyl, pyronecarbonyl, thiopyronecarbonyl, pyridonecarbonyl, and aromatic carbocyclic or heterocyclic acyl optionally substituted by e.g. halogen, trifluoromethyl, 1-5C alkyl, 1-5C aminoalkyl, 1-5C hydroxyalkyl; trityl, and other amino-protecting groups) or protected amino in the form of phthalimino or enamino derived from acetoacetates, acetylacetone, acetoacetonitrile, and like protecting groups;
  ii. hydroxy, 1-3C alkoxy, or 1-5C acyloxy;
  iii. carboxy, 2-10C alkoxycarbonyl, indanyloxycarbonyl, phenoxycarbonyl, dimethylphenoxycarbonyl, or like groups; or
  iv. azido, cyano, carbamoyl, sulfo, 1-5C alkoxysulfonyl, 1-3C alkoxyphosphonyl, or like groups);

8. 3-5C 2-syndon-3-alkanoyl;
9. 6-8C (2- or 4-pyridon-1-yl)alkanoyl;
10. 5-aminoadipoyl, 5-aminoadipoyl protected at the amino or carboxy;
11. acyls of the formula:

(where L is an easily removable 1-10C hydrocarbyl e.g. 2,2,2-trichloroethyl, isobornyl, t-butyl, 1-methylcyclohexyl, 2-alkoxy-t-butyl, benzyl, p-nitrobenzyl, p-methoxybenzyl, benzhydryl), and the like acyls.

Typical examples of Ar in the said definition include furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, and dihydrophenyl, each optionally may be substituted by e.g. halogen, 1-5C alkyl, hydroxy, aminomethyl, or 1-3C alkoxy.

Preferable Acyls are those of naturally occuring penicillins i.e. phenylacetyl or phenoxyacetyl.

COB in Compounds (I) is carboxy or protected carboxy. Representatives of them include those constituting esters [1-5C alkyl (e.g. methyl, ethyl, trichloroethyl, t-butyl esters), 7-20C aralkyl (e.g. benzyl, methoxybenzyl, nitrobenzyl, diphenylmethyl, trityl esters), 6-12C aryl (e.g. phenyl and naphthyl esters), metal (e.g. trimethylsilyl, methoxydimethylsilyl, trimethylstannyl esters), and other esters], acid anhydrides, salts (e.g. sodium, potassium, magnesium, aluminum salts), thiol esters, amides, hydrazides, azides, and other derivatives of carboxy groups. COB can, where possible, have substituents referred to above e.g. halogen, sulfur-, oxygen-, nitrogen-, carbon-, or other functions or can be unsaturated.

Among these protected carboxy, important groups for COB are those inert to the reaction and removable after the reaction without adverse effect on the other part of the molecule (e.g. 1-3C haloalkyl, 2-10C acylalkyl, 2-7C alkoxyalkyl, 2-7C acyloxyalkyl, 7-20C aralkyl esters, 2-6C dialkylhydrazides, alkali metal salts, and 1-12C alkylamine salts).

The protecting group in COB has no meaning other than protection and deprotection, and wide variation can be possible without changing the gist of this invention.

Preferable COB groups include benzhydryloxycarbonyl, benzyloxycarbonyl, p-methoxybenzyloxycarbonyl, p-nitrobenzyloxycarbonyl, and 2,2,2-trichloroethoxycarbonyl.

X in Compounds (I) is hydrogen or nucleophilic group. The nucleophilic group can be halogen, acyloxy, hydroxy, mercapto, 1-3C alkylthio, 1-6C arylthio including heteroaromatic thio represented by partial formula:

Ar—S—

(where Ar is defined above)

and other nucleophilic groups bound to methyl at position 3 of cephem ring in known cephalosporins. It can be exemplified by halogen (e.g. chlorine, bromine, fluorine), acyloxy (e.g. formyloxy, acetyloxy, propionyloxy, benzoyloxy, carbonic or sulfuric acyloxy), 1-3C alkoxy (e.g. methoxy, ethoxy, butoxy), arylthio (e.g. phenylthio, nitrophenylthio, tolylthio, 1,3,4-thiadiazolylthio, 2-methyl-1,3,4-thiadiazol-5-ylthio, 2-hydroxymethyl-1,3,4-thiadiazol-5-ylthio, 1-methyltetrazol-5-ylthio, 1,2,3-triazol-5-ylthio, pyridazin-3-ylthio, 1-oxidopyridin-2-yl-thio) or like nucleophiles.

Preferable X groups include hydrogen, chlorine, 1-5C alkanoyloxy, 1,3,4-thiadiazol-5-ylthio, 2-methyl-1,3,4-thiadiazol-5-ylthio, and 1-methyltetrazol-5-ylthio.

When a group Acyl, X, or COB is unstable under the reaction condition, it can be protected prior to and deprotected after the reaction to avoid unfavorable side reactions.

Typical and specific examples of Compounds (I) are:

6β-(N-nitroso-phenylacetamido)-2α-methyl-2β-chloromethylpenam-3α-carboxylic acid diphenylmethyl ester 1α-oxide,
6β-(N-nitroso-phenylacetamido)-2α-methyl-2β-acetoxymethylpenam-3α-carboxylic acid 2,2,2-trichloroethyl ester 1α-oxide,
6β-(N-nitroso-phenoxyacetamido)penicillanic acid diphenylmethyl ester 1α-oxide,
6β-(N-nitroso-phenoxyacetamido)-2α-methyl-2β-chloromethylpenam-3α-carboxylic acid diphenylmethyl ester 1α-oxide,
6β-(N-nitroso-phenoxyacetamido)-2α-methyl-2β-acetoxymethylpenam-3α-carboxylic acid diphenylmethyl ester 1α-oxide, and
6β-(N-nitroso-phenoxyacetamido)-2α-methyl-2β-acetoxymethylpenam-3α-carboxylic acid benzyl ester 1α-oxide.

Starting materials for preparing Compounds (I) can be prepared by treating a 6-acylaminopenicillanic acid or its derivative with a nitroso-introducing reagent (particularly nitrogen dioxides i.e. dinitrogen tetroxide, dinitrogen trioxide, nitrosyl halide, alkyl nitrite).

Compounds (I) can be prepared, for example, by the action of an oxidizing reagent on the starting material (II), 6-(N-nitroso-N-acylamino)-penicillanic acid or its derivative, according to the following scheme:

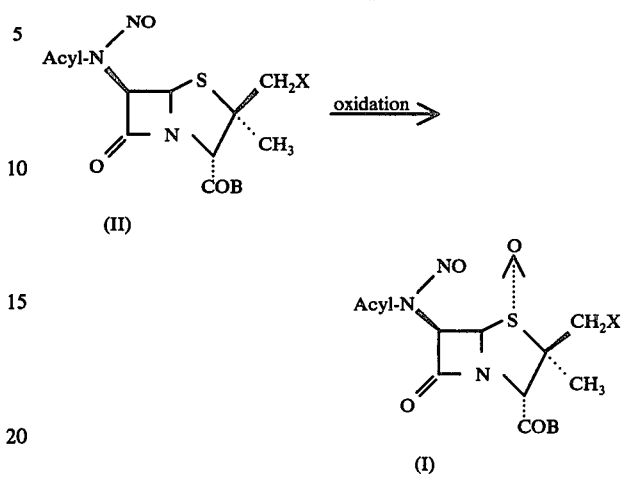

(where COB and X are defined above).

Said oxidizing reagent is that capable of oxidizing a sulfide to give a sulfoxide, for example, organic or inorganic peracids of oxido-reduction potential higher than +0.7 (especially m-chloroperbenzoic acid, perbenzoic acid, monoperphthalic acid, peracetic acid, periodic acid), or their salts, hydrogen peroxide, urea peroxide, nickel peroxide, and like oxidative reagents, if required in the presence of catalyzer (e.g. wolfrumates for hydrogen peroxide).

The reaction is preferably carried out in a solvent (particularly hydrocarbon-, halohydrocarbon-, ether-, ester-, ketone-, nitrohydrocarbon-, water-, alcohol-solvents or their mixtures), especially methylene chloride.

Under more drastic conditions, sulfones can be obtained as by-products.

Usually, a temperature over 50° C should be avoided to minimize formation of azo compounds by removal of acyl.

The reaction is completed usually within 0.5 to 10 hours. The products can be isolated by conventional methods. As the products are unstable, they are preferably stored after removing the nitroso group by successive reduction.

Compounds (I) can be used for preparing penicillin 1α-oxides (III) difficultly prepared until this invention. The process comprises treatment of Compound (I) with a reducing reagent capable of converting N-nitroso to NH without causing undesirable changes on other parts of the molecule (particularly, reducing metals e.g. aluminum, zinc, tin, or iron, and acid; hydrosulfite; boranic acid derivatives; and like reagents) according to the following reaction scheme:

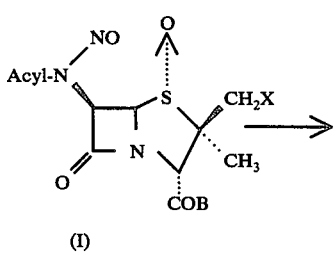

-continued

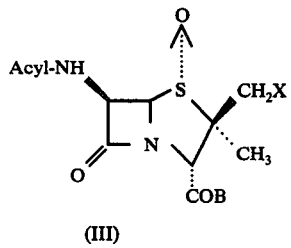

(where COB and X are defined above)

The reaction is carried out in a solvent as described above in relation to the preparation of Compounds (I), and is generally completed within 0.1 to 5 hours at room temperature to 0° C.

The products can be isolated by conventional manners from the reaction mixture.

These two reactions can be carried out in one reaction vessel without separation and purification of the intermediates (I) for convenient procedures and safer handling of unstable intermediates. Thus, Compounds (III) are now preparable from Compounds (II) in more than 60% over-all yield, by simple treatment.

Compounds (III) (and therefore Compounds (I)) are useful for preparing known antibacterial cephalosporins including cefalotin and cefazolin, by successive treatment with e.g. benzothiazol-2-thiol; halogen; and then heating, to give recyclized cephem compounds. Thus, the reactions constitute a synthesis of expensive cephalosporins from less expensive penicillins.

The following examples are provided to illustrate this invention in detail, but they are not intended to restrict the scope thereof. Elemental analyses and physical constants of the products are not contradictory to given structures.

EXAMPLE 1

Table I shows examples of reaction conditions, and Tables II A to C show physical constants of the products.

Among them, the first example is described below to show more detailed procedures. Other examples are carried out analogously.

(The First Example in Table I)

(1) To a solution of benzhydryl 6-phenylacetamido-2β-chloromethyl-2α-methylpenam-3α-carboxylate (11.6 g) in methylene chloride (25 ml) are added sodium acetate (5 g) and nitrogen dioxide (2 ml), and the mixture stirred at 0° C for 40 minutes. The reaction mixture is poured into ice water containing sodium hydrogen carbonate and extracted with methylene chloride. The extract is washed with water, dried, and concentrated to give diphenylmethyl 6-(N-nitroso-N-phenylacetylamino)-2β-chloromethyl-2α-methylpenam-3α-carboxylate (11.8 g).

(2) To a solution of the product (11.8 g) prepared above (1) in methylene chloride (120 ml) is added m-chloroperbenzoic acid (4.5 g) at 0° C, and the mixture stirred for 2 hours. The reaction mixture is poured into ice-water and extracted with methylene chloride. The extract is washed with cold 1N-sodium carbonate solution and water, dried, and concentrated to give diphenylmethyl 6-(N-nitroso-N-phenylacetylamino)-2β-chloromethyl-2α-methylpenam-3α-carboxylate 1α-oxide (11.2 g).

(3) To a solution of the product (11.2 g) prepared above (2) in methylene chloride (200 ml) are added acetic acid (20 ml) and zinc powder (8 g), and the mixture stirred at 0° C for 1 hour. After filtering off the insoluble material, the methylene chloride layer is washed with water, dried, and concentrated to give diphenylmethyl 6β-phenylacetamido-2β-chloromethyl-2α-methylpenam-3α-carboxylate 1α-oxide (9.59 g). This product is chromatographed on 10% water-silica gel (200 g) to give pure product (6.32 g).

TABLE I

Reaction Conditions (IV) → (II) [NaOCCH₃, NO₂] → (I) [m-CPBA] → (III) [Zn, CH₃COH]

| No. | R¹ | R² | X | (IV) (g) | CH₂Cl₂ (ml) | NaOCOCH₃ (g) | NO₂ (ml) | temp (°C) | time (min) | (II) (g) | CH₂Cl₂ (ml) | m-CPBA (g) | temp (°C) | time (hr) | (I) (g) | CH₂Cl₂ (ml) | Zn (g) | CH₃COOH (ml) | temp (°C) | time (hr) |
|---|---|---|---|---|---|---|---|---|---|---|---|---|---|---|---|---|---|---|---|---|
| 1 | PhCH₂— | —CHPh₂ | —Cl | 11.6 | 25 | 5 | 2 | 0 | 40 | 11.8 | 120 | 4.5 | 0 | 2 | 11.2 | 200 | 8 | 20 | 0 | 1 |
| 2 | PhOCH₂— | —CHPh₂ | —Cl | 1.8 | 6 | 2 | 2 | 0 | 90 | 2.0 | 70 | 0.8 | 0 | — | — | 70 | 2 | 8 | 0 | 1 |
| 3 | PhOCH₂— | —CHPh₂ | —OCCH₃(=O) | 7 | 30 | 3 | 3 | — | 60 | — | 30 | 3 | — | 1.5 | — | 30 | 5 | 2 | 0 | 1 |
| 4 | PhCH₂— | —CH₂CCl₃ | —OCCH₃(=O) | 1.15 | 6 | 1 | 0.5 | 0 | 60 | — | 6 | 0.48 | — | — | — | 6 | 1 | 0.5 | 0 | 1 |
| 5 | PhCH₂— | —CH₂Ph | —OCCH₃(=O) | 4.84 | 10 | 4 | 0.5 | 0 | 60 | — | 10 | 2.05 | — | — | — | 10 | 5 | 2 | — | — |
| 6 | PhOCH₂— | —CHPh₂ | —H | 1.0 | 10 | 2 | 1 | 0 | 120 | 1.06 | 20 | 0.42 | 0 | 0.75 | 1.1 | 20 | 1.5 | 5 | 0 | 1 |

(Abbreviations) Ph = Phenyl; m-CPBA = m-chloroperbenzoic acid.

TABLE II A

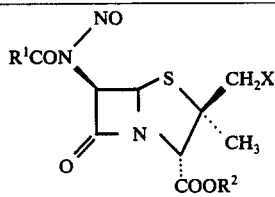

(II)

| No. | R¹ | R² | X | IR: $\nu_{max}^{CHCl_3}$ cm$^{-1}$ | NMR: $\delta^{CDCl_3}$ (Hz-values show coupling constants) |
|---|---|---|---|---|---|
| 1 | PhCH₂— | —CHPh₂ | —Cl | 1800,1750,1600, 1490. | 1.51s3H,4.02ABq(12,30Hz)2H,5.3s1H,5.5m4H,5.8–7.6m15H. |
| 2 | PhOCH₂— | —CHPh₂ | —Cl | — | — |
| 3 | PhOCH₂— | —CHPh₂ | —OCCH₃ ‖ O | 1800,1745. | 1.22s3H,2.10s3H,4.38q(6;9Hz)2H,5.05s1H,5.50s2H,5.75d(2Hz)1H. |
| 4 | PhCH₂— | —CH₂CCl₃ | —OCCH₃ ‖ O | 1800,1745–1765. | 1.50s3H,2.10s3H,4.40q(6;9Hz)2H,4.50s2H,4.80s2H,5.05s1H, 5.70d(2Hz)1H,7.35s5H. |
| 5 | PhOCH₂— | —CH₂Ph | —OCCH₃ ‖ O | 1800,1750. | 1.34s3H,2.05s3H,4.40q(6;9Hz)2H,4.98s1H,5.29s2H,5.55s2H, 5.76d(2Hz)1H. |
| 6 | PhOCH₂— | —CHPh₂ | —H | 1800,1755. | 1.20s3H,1.63s3H,4.64s1H,5.40s2H,5.18d(2.5Hz)1H,5.61d(2.5Hz)1H. |

TABLE II B

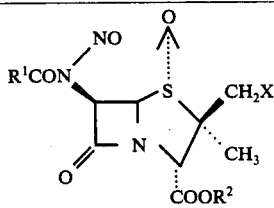

(I)

| No. | R¹ | R² | X | IR: $\nu_{max}^{CHCl_3}$ cm$^{-1}$ | NMR: $\delta^{CDCl_3}$ (Hz-values show coupling constants) |
|---|---|---|---|---|---|
| 1 | PhCH₂— | —CHPh₂ | —Cl | 1810,1750,1600, 1490. | 1.13s3H,3.98s2H,5.0s1H,5.63s2H,5.4ABq(79;3Hz)2H,6.8–7.6m15H. |
| 2 | PhOCH₂— | —CHPh₂ | —Cl | — | — |
| 3 | PhOCH₂— | —CHPh₂ | —OCCH₃ ‖ O | 1810,1750. | 1.00s3H,2.09s3H,4.50q(6;9Hz)2H,5.00s1H,5.57s2H,6.17d(2.5Hz)1H. |
| 4 | PhCH₂— | —CH₂CCl₃ | —OCCH₃ ‖ O | 1810,1755–1780. | 1.32s3H,2.03s3H,4.59q(6;9Hz)2H,6.10(2Hz)1H,6.35s5H. |
| 5 | PhOCH₂— | —CH₂Ph | —OCCH₃ ‖ O | 1810,1750. | 1.10s3H,2.02s3H,4.43q(6;10Hz)2H,4.87s1H,5.30s2H,5.53s2H, 6.10d(2.5Hz)1H. |
| 6 | PhOCH₂— | —CHPh₂ | —H | 1810,1755. | 1.01s3H,1.72s3H,4.67d(2.5Hz)1H,4.68s1H,5.51s2H,6.10d(2.5Hz)1H. |

TABLE II C

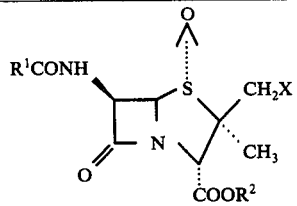

(III)

| No. | R¹ | R² | X | IR: $\nu_{max}^{CHCl_3}$ cm$^{-1}$ | NMR: $\delta^{CDCl_3}$ (Hz-values show coupling constants) |
|---|---|---|---|---|---|
| 1 | PhCH₂— | —CHPh₂ | —Cl | 3425,1800,1750, 1695,1600,1595. | 1.1s3H,4.5s2H,4.86s1H,4.76d(4Hz)1H,5.33q(7Hz)1H,6.93m1H, 6.8–7.6m15H. |
| 2 | PhOCH₂— | —CHPh₂ | —Cl | 1800,1745,1692. | 1.20s3H,3.98s2H,4.0s2H,4.90d(2Hz)1H,5.00s1H,5.42q1H. |
| 3 | PhOCH₂— | —CHPh₂ | —OCCH₃ ‖ O | 1800,1750,1700. | 1.10s3H,2.17s3H,4.50s2H,4.63s2H,4.90s1H,4.92d(2Hz)1H, 5.62q(2;4Hz)1H. |
| 4 | PhCH₂— | —CH₂CCl₃ | —OCCH₃ ‖ O | 1800,1750,1680. | 1.37s3H,2.00s3H,3.60s2H,4.50s2H,4.68d(7Hz)1H,4.75d(2Hz)1H, 4.92d(7Hz)1H,5.19q(2;4Hz)1H. |

TABLE II C-continued

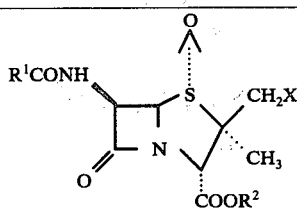

(III)

| No. | R¹ | R² | X | IR: $\nu_{max}^{CHCl_3}$ cm$^{-1}$ | NMR: $\delta^{CDCl_3}$ (Hz-values show coupling constants) |
|---|---|---|---|---|---|
| 5 | PhOCH$_2$— | —CH$_2$Ph | —OCCH$_3$ ‖ O | 1800,1750,1695. | 1.22s3H,2.05s3H,4.43s2H,4.60s2H,4.78s1H,4.90d(2Hz)1H,5.30s2H, 5.50q(2;4Hz)1H. |
| 6 | PhOCH$_2$— | —CHPh$_2$ | —H | 3420,1800,1755, 1700. | 1.05s3H,1.62s3H,4.55s1H,4.58s2H,4.79d(2.5Hz)1H,5.57q(2.5;4Hz)1H. |

What we claim is:

1. A compound of the formula

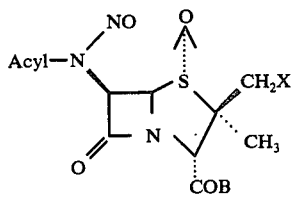

wherein Acyl is (1) 1-5C alkanoyl, (2) 2-5C haloalkanoyl, (3) azidoacetyl, (4) cyanoacetyl, (5) Ar—CQQ'—CO— in which Q and Q' each is hydrogen or methyl, and Ar is furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl or dihydrophenyl, each Ar being unsubstituted or substituted by 1-5C alkyl, 1-5C alkoxy, halogen, trifluoromethyl, hydroxy, cyano, aminomethyl, nitroso or nitro, (6) Ar—G—CQQ'—CO— in which G is oxygen or sulfur, and Ar, Q and Q' are as defined above, (7) Ar—CHT—CO— in which Ar is as defined above, and T is amino, ammonio, protected amino, hydroxy, 1-3C alkoxy, 1-5C acyloxy, carboxy, 2-10C alkoxycarbonyl, indanyloxycarbonyl, phenoxycarbonyl, dimethylphenoxycarbonyl, azido, cyano, carbamoyl, sulfo, 1-5C alkoxysulfonyl or 1-3C alkoxyphosphonyl, (8) 3-5C 2-syndon-3-alkanoyl, (9) 6-8C (2- or 4-pyridon-1-yl)alkanoyl, (10) 5-aminoadipoyl, (11) 5-aminoadipoyl protected at the amino and/or carboxy, or (12) L—O—CO— in which L is 2,2,2-trichloroethyl, isobornyl, t-butyl, 1-methylcyclohexyl, 2-alkoxy-t-butyl, benzyl, p-nitrobenzyl, p-methoxybenzyl or benzhydryl, COB is carboxy or protected carboxy, X is hydrogen, chlorine, bromine, fluorine, formyloxy, acetyloxy, propionyloxy, benzoyloxy, carbonic acid acyloxy, sulfuric acid acyloxy, methoxy, ethoxy, butoxy, phenylthio, nitrophenylthio, tolylthio, 1,3,4-thiadiazolylthio, 2-methyl-1,3,4-thiadiazol-5-ylthio, 2-hydroxymethyl-1,3,4-thiadiazol-5-ylthio, 1-methyltetrazol-5-ylthio, 1,2,3-thiazol-5-ylthio, pyridazin-3-ylthio or 1-oxidopyridin-2-ylthio.

2. A compound according to claim 1, wherein Acyl is phenylacetyl or phenoxyacetyl.

3. A compound according to claim 1, wherein COB is carboxy, benzhydryloxycarbonyl, benzyloxycarbonyl, p-methoxybenzyloxycarbonyl, p-nitrobenzyloxycarbonyl or 2,2,2-trichloroethoxycarbonyl.

4. A compound according to claim 1, wherein X is hydrogen, chlorine, formyloxy, acetyloxy, propionyloxy, 1,3,4-thiadiazol-5-ylthio, 2-methyl-1,3,4-thiadiazol-5-ylthio or 1-methyltetrazol-5-ylthio.

5. The compound according to claim 1, namely 6β-(N-nitroso-phenylacetamido)-2α-methyl-2β-chloromethylpenam-3α-carboxylic acid diphenylmethyl ester 1α-oxide.

6. The compound according to claim 1, namely 6β-(N-nitroso-phenylacetamido)-2α-methyl-2β-acetoxymethylpenam-3α-carboxylic acid 2,2,2-trichloroethyl ester 1α-oxide.

7. The compound according to claim 1, namely 6β-(N-nitroso-phenoxyacetamido)penicillanic acid diphenylmethyl ester 1α-oxide.

8. The compound according to claim 1, namely 6β-(N-nitroso-phenoxyacetamido)-2α-methyl-2β-chloromethylpenam-3α-carboxylic acid diphenylmethyl ester 1α-oxide.

9. The compound according to claim 1, namely 6β-(N-nitroso-phenoxyacetamido)-2α-methyl-2β-acetoxymethylpenam-3α-carboxylic acid diphenylmethyl ester 1α-oxide.

10. The compound according to claim 1, namely 6β-(N-nitroso-phenoxyacetamido)-2α-methyl-2β-acetoxymethylpenam-3α-carboxylic acid benzyl ester 1α-oxide.

* * * * *